(12) United States Patent
Müller et al.

(10) Patent No.: US 11,806,251 B2
(45) Date of Patent: Nov. 7, 2023

(54) IMPACT INSTRUMENT

(71) Applicants: ENDOCON GMBH, Neckargemünd (DE); UNIVERSITÄTSKLINIKUM HEIDELBERG, Heidelberg (DE)

(72) Inventors: Ulrike Müller, Solothurn (CH); Jan Philippe Kretzer, Heidelberg (DE); Klaus Notarbartolo, Wiesenbach (DE); Robert Lingslebe, Heidelberg (DE)

(73) Assignees: ENDOCON GMBH, Wiesenbach (DE); UNIVERSITÄTSKLINIKUM HEIDELBERG, Heidelberg (DE)

( * ) Notice: Subject to any disclaimer, the term of this patent is extended or adjusted under 35 U.S.C. 154(b) by 348 days.

(21) Appl. No.: 17/284,015

(22) PCT Filed: Oct. 8, 2019

(86) PCT No.: PCT/EP2019/077203
§ 371 (c)(1),
(2) Date: Apr. 9, 2021

(87) PCT Pub. No.: WO2020/074501
PCT Pub. Date: Apr. 16, 2020

(65) Prior Publication Data
US 2021/0378840 A1    Dec. 9, 2021

(30) Foreign Application Priority Data
Oct. 11, 2018    (DE) .......................... 102018125190.4

(51) Int. Cl.
*A61F 2/46*    (2006.01)
*A61F 2/30*    (2006.01)

(52) U.S. Cl.
CPC .............. *A61F 2/46* (2013.01); *A61F 2/4603* (2013.01); *A61F 2002/30649* (2013.01); *A61F 2002/4627* (2013.01); *A61F 2002/4681* (2013.01)

(58) Field of Classification Search
CPC ........ A61F 2/46; A61F 2/4603; A61F 2/4607; A61F 2/4637; A61F 2/4609;
(Continued)

(56) References Cited

U.S. PATENT DOCUMENTS 2,787,178 A * 4/1957 Maxim .................... B25D 5/02
30/367
3,074,155 A * 1/1963 Hahn ................. H05K 13/0447
81/463
(Continued)

FOREIGN PATENT DOCUMENTS

DE       60104499       8/2005
DE     202006000845     4/2006
(Continued)

OTHER PUBLICATIONS

Official Action with machine translation for German Patent Application No. 102018125190.4, dated May 28, 2019, 14 pages.
(Continued)

*Primary Examiner* — Tracy L Kamikawa
(74) *Attorney, Agent, or Firm* — Sheridan Ross P.C.

(57) ABSTRACT

Impact instrument for joining prosthetic implants, comprising a housing which accommodates a striker pin, a first spring element associated with the striker pin, a release device and, at least in part, a striking piece, wherein the striking piece projects from the housing at an end face, wherein the release device is movable between a fixing position and a release position, wherein the striker pin is spaced apart from the striking piece the fixing position,
(Continued)

wherein the release device moves automatically from the fixing position to the release position when the striking piece moves axially into the housing, in order to release the striker pin once the release position has been reached, so that the latter moves in the direction of the striking piece, accelerated by the first spring element.

14 Claims, 2 Drawing Sheets

(58) Field of Classification Search
CPC ...... A61F 2002/4627; A61F 2002/4681; A61F 2002/4625; A61B 17/92; A61B 2017/922; A61B 2017/925; A61B 2017/928; B25B 19/00; B25B 21/00; B25B 21/02; B25B 21/008; B25B 21/026
See application file for complete search history.

(56) References Cited

U.S. PATENT DOCUMENTS

| | | | | |
|---|---|---|---|---|
| 3,385,380 | A | * | 5/1968 | Waller .................. B25B 27/143 81/463 |
| 5,632,765 | A | * | 5/1997 | Holder .................. A61H 23/06 601/108 |
| 7,708,739 | B2 | * | 5/2010 | Kilburn ................. A61F 2/4612 606/86 R |
| 8,650,988 | B2 | * | 2/2014 | Yen ...................... H02G 1/1209 81/9.41 |
| 9,005,213 | B2 | | 4/2015 | Fortin et al. |
| 10,231,848 | B2 | | 3/2019 | Biegun et al. |
| 2014/0142583 | A1 | | 5/2014 | Fortin et al. |
| 2015/0094728 | A1 | | 4/2015 | Rhoades et al. |

FOREIGN PATENT DOCUMENTS

| | | |
|---|---|---|
| DE | 102016101900 | 8/2017 |
| EP | 3181067 | 6/2017 |

OTHER PUBLICATIONS

International Search Report and Written Opinion for International (PCT) Patent Application No. PCT/EP2019/077203, dated Feb. 3, 2020, 8 pages.

Translation of the International Search Report for International (PCT) Patent Application No. PCT/EP2019/077203, dated Feb. 3, 2020, 2 pages.

International Preliminary Report on Patentability for International (PCT) Patent Application No. PCT/EP2019/077203, dated Apr. 8, 2021, 6 pages.

* cited by examiner

IMPACT INSTRUMENT

CROSS REFERENCE TO RELATED APPLICATIONS

This application is a national stage application under 35 U.S.C. 371 and claims the benefit of PCT Application No. PCT/EP2019/077203 having an international filing date of 8 Oct. 2019, which designated the United States, which PCT application claimed the benefit of German Patent Application No. 102018125190.4 filed 11 Oct. 2018, the disclosure of each of which are incorporated herein by reference.

BACKGROUND OF THE INVENTION

The invention relates to an impact instrument for joining prosthetic implants, comprising a housing which accommodates a striker pin, wherein a first spring element is associated with the striker pin, wherein the striker pin is fixed in the housing by means of a latching device, wherein the first spring element accelerates the striker pin in the direction of a striking piece after release of the latching device and introduces an impulse into the striking piece.

Such an impact instrument is known from DE 20 2006 000 845 U1. The impact instrument is primarily used to attach an implant component, such as a joint ball, to a conical clamping pin of another implant component. The impact instrument known from prior art allows the application of a predetermined impulse which depends almost exclusively on the spring force of the spring that is integrated in the impact instrument.

One problem, however, is that the previously known impact instrument must be manually preloaded. Releasing is done by pressing a release button. Thereafter, although a striker pin is accelerated and exerts a predetermined impulse on a striking piece, this is done independently of the positioning of the striking piece on the implant component to be attached. This does not ensure that the impulse exerted by the striker pin on the striking piece is completely transferred by the striker pin onto the implant component to be joined.

BRIEF SUMMARY OF THE INVENTION

The object of the invention is to provide an impact instrument which enables reproducible impulse exertion onto an implant component to be joined while being easy to handle.

This object is achieved using the features of claim 1. The dependent claims make reference to advantageous embodiments.

The impact instrument according to the invention for joining prosthetic implants comprises a housing which accommodates a striker pin, a first spring element associated with the striker pin, a release device and at least partially a striking piece, wherein the striking piece protrudes from the housing at one end face, wherein the release device is movable between a fixing position and a release position, wherein the striking pin is spaced apart from the striking piece in the fixing position, wherein the release device moves automatically from the fixing position to the release position upon an axial movement of the striking piece into the housing, in order to release the striking pin after reaching the release position, so that the striking pin moves accelerated by the first spring element in the direction of the striking piece.

Accordingly, the striking pin is released automatically depending on the position of the striking piece relative to the housing. In particular, the impact instrument according to the invention does not require the manual operation of a release lever, a push button, or the like. To join prosthetic implants, the user places the striking piece on the prosthetic implant to be joined and moves the housing in the axial direction towards the prosthetic implant. Thereby, the striking piece moves into the housing, wherein the release device is moved from the fixing position into the release position, wherein, after reaching the release position, the striker pin is released and moves, accelerated by the first spring element, in the direction of the striking piece in order to introduce an impulse into the striking piece there. The fact that the release device is only moved into the release position when the striking piece moves into the housing ensures that the impact instrument, or the striking piece, is firmly and securely placed on the prosthetic implant. Here, it is advantageous that the impulse introduced into the striking piece by the striker pin is completely transferred from the striking piece to the prosthetic implant. The force acting on the prosthetic implant during movement of the impact instrument or the release device between the fixing position and the release position is always the same. This makes it possible to introduce a reproducible impulse into the prosthetic implant, wherein the impulse corresponds exactly to the impulse required for joining.

The impact instrument according to the invention is thus particularly suitable for joining conical connections or tapered interference fits, which are frequently used in particular in the field of endoprosthetics, for example in hip prostheses. There, a ceramic or metallic ball is placed on a cone of a hip implant. Until now, the ball has usually been attached to the implant by a single hammer blow.

When attaching the element by means of a hammer blow, it is particularly problematic that the force of the hammer blow is not reproducible. If the applied impulse is not great enough, the ball may not be adequately attached to the hip implant. This can cause micromovements between the ball and the shaft, wherein metal ions are released that can damage the surrounding tissue. If the impulse exerted is too great, damage can occur to the bone into which the shaft is inserted.

In view of this, the impact instrument according to the invention is particularly advantageous because, in order to release the impact instrument, a pre-tensioning of the striking piece on the element to be fastened is provided. After reaching the release position, the striker pin is released abruptly and an impulse with a very short impulse duration is applied to the components of the implant to join the connection.

The release device may comprise a first sleeve which is arranged in the housing in an axially movable manner and accommodates the striker pin, wherein the first sleeve comprises at least one opening at the circumference, wherein at least one locking body is arranged in the opening. In this embodiment, the release mechanism is accommodated in the housing and is directly associated with the striker pin.

The striker pin may have at least one recess which accommodates the locking body in the fixing position. The locking body accommodated in the recess causes the striker pin to be fixed in the fixing position relative to the first sleeve.

The recess may be in the form of a circumferential groove formed in the circumference of the striker pin. A circumferential groove is, on the one hand, easy to produce and, on the other hand, allows rotational movements of the striker pin. This can prevent the striker pin from jamming in the first sleeve.

The locking body may abut against the inner wall of the housing in the fixing position, wherein the inner diameter of the housing is selected such that the locking body is retained in the opening of the first sleeve and in the recess of the striker pin, thereby locking the striker pin relative to the first sleeve. The housing comprises a through bore, wherein the inner diameter of the through bore in this embodiment is selected such that the first sleeve abuts against the inner wall of the bore with its outer wall. As a result, the locking bodies are fixed in the opening and in the recess of the striker pin, so that the striker pin is locked relative to the first sleeve.

The locking bodies are preferably formed in the form of spheres, wherein the first sleeve has several of openings, preferably three openings distributed over the circumference in the form of bores, which accommodate the spherical locking bodies. Spherical locking bodies are particularly advantageous, as they can roll against the inner wall of the housing and do not tend to jam.

The striking piece can axially move the first sleeve and the striker pin locked with the first sleeve within the housing as the striking piece moves into the housing in axial direction. When the impact instrument is placed on the implant to be joined, a force is applied to the impact instrument, causing the striking piece to move into the housing. At the same time, the first sleeve and the striker pin locked with the first sleeve are moved.

The housing may be provided with a cross-section expansion, wherein the internal diameter of the housing increases in the region of the cross-section expansion, wherein the cross-section expansion is configured to partially accommodate the locking body in the release position.

The cross-section expansion is preferably in the form of a conical step, which is provided in the inner wall of the housing. When the impact instrument is pressed onto the implant to such an extent that the locking body fixed in the first sleeve reaches the area of the cross-section expansion, the locking body slides out of the recess of the impact instrument and into the cross-section expansion. This releases the striker pin. In this respect, the area of the cross-section expansion corresponds to the release position.

The first sleeve may have a receiving part for the striking piece on one end face, wherein the receiving part is configured such that the striker pin contacts the striking piece directly in the release position. This ensures that the impulse of the accelerated striker pin can be fully transferred into the striking piece.

The striker pin may be provided with a circumferential collar, wherein the first spring element bears against the collar and against the housing. In this embodiment, the first spring element is securely fixed to the striker pin.

A second sleeve may be arranged between the first sleeve and the housing, wherein the inner wall of the second sleeve forms a sliding surface for the locking body, and wherein the cross-section expansion is provided in the second sleeve. In this embodiment, the locking body slides along the inner wall of the second sleeve. In particular, the locking body does not contact the inner wall of the housing. The fixing position and the release position are thereby represented by the design of the inner wall of the second sleeve and the arrangement of the locking bodies relative to the second sleeve.

The second sleeve may be accommodated in the housing in an axially movable manner, and a second spring element may be provided to position the second sleeve relative to the housing. The second spring element causes the second sleeve to move until the opening, the locking bodies and the recess are aligned, thereby causing the locking bodies to slide back into the recess and thus to lock the striker pin with the first sleeve.

A third spring element may be provided, which is arranged on the end face side of the first sleeve and on the housing and which, in the fixing position, spaces the striker pin and the striking piece apart from one another. The third spring element ensures that the first sleeve and the striking piece are returned to the release position.

The housing may be provided with a handpiece. The handpiece improves the operability of the impact instrument.

At least one sealing element may be arranged between the housing and the striking piece.

According to an alternative embodiment, a sleeve is rotatably arranged in the housing, wherein the sleeve has at least one L-shaped opening and an inclined plane. A driver engages in the opening, which driver slides along the inclined plane during axial movement of the housing relative to the striking piece and thus causes the sleeve to turn. A retaining pin is also arranged in the sleeve, which is assigned to the striker pin. The retaining pin initially slides along the horizontal section of the L-shaped opening during axial movement of the housing and is released after reaching the edge, the transition between the horizontal and vertical sections of the opening. In this process, the striker pin is accelerated in the direction of the striking piece by the spring element associated with the striker pin and an impulse is exerted onto the implant to be joined. A return spring automatically returns the components to their original position after unloading.

Some embodiments of the impact instrument according to the invention are explained in more detail below with reference the figures. These show, in each case schematically:

DETAILED DESCRIPTION OF THE INVENTION

Figure 1:
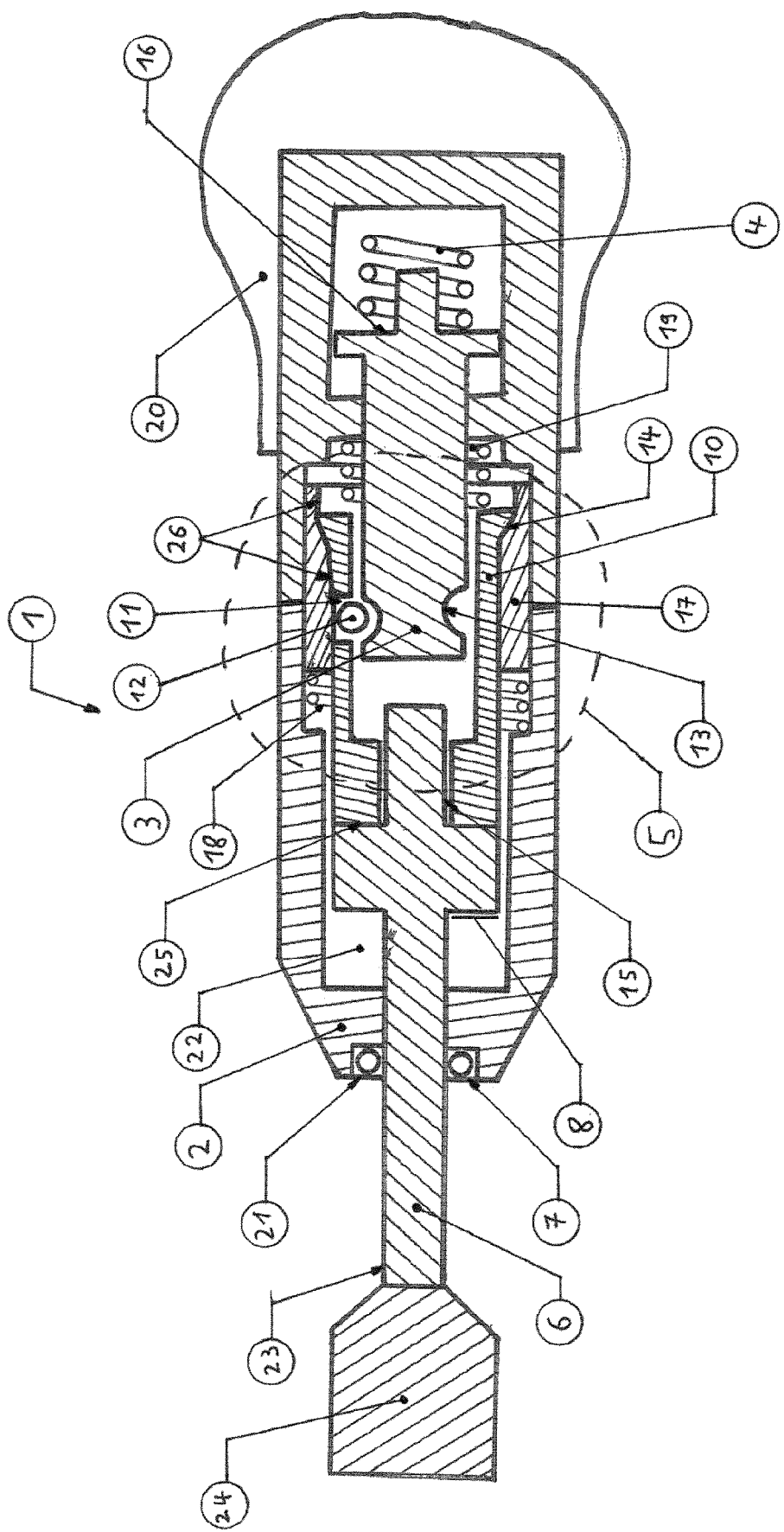
FIG. 1 a cross-section view of the impact instrument in the fixing position.

The figures show an impact instrument 1 for joining prosthetic implants. The impact instrument 1 is used in particular for joining tapered interference fits, which are frequently used in endoprosthetics in general. In the present embodiment, the impact instrument 1 is used for joining joint balls to a conical clamping pin of a hip implant. However, it is also conceivable that the impact instrument 1 is used for joining knee prostheses, shoulder prostheses or the like.

The impact instrument 1 comprises a housing 2 made of metallic material, wherein the housing 2 is provided with a through bore 22. The housing 2 accommodates a striker pin 3, a first spring element 4 assigned to the striker pin 3, a release device 5 and, in part, a striking piece 6. The striking piece 6 protrudes from the housing 2 at one end face of the housing 2.

The striker pin 3, the first spring element 4 and the striking piece 6 are also made of metallic material.

The release device 5 is movable between a fixing position 8 and a release position 9, wherein the striker pin 3 is spaced apart from the striking piece 6 in the fixing position 8. When the striking piece 6 is moved axially into the housing 2, the release device 5 moves automatically from the fixing position 8 to the release position 9.

After reaching the release position 9, the striker pin 3 is released so that it moves accelerated by the first spring element 4 towards the striking piece 6.

The release device 5 has a first sleeve 10, which is arranged in the bore 22 of the housing 2 in an axially movable manner, wherein the first sleeve 10 accommodates the striker pin 3, wherein the first sleeve 10 has three openings 11 distributed over the circumference. A locking body 12 in the form of a metal ball is arranged in each of the openings 11. The first sleeve 10 is also made of metallic material.

A recess 13 in the form of a circumferential groove is formed in the striker pin 3, wherein the locking bodies 12 are locked in the recess 13 in the fixing position 8.

A second sleeve 17 is arranged between the first sleeve 10 and the housing 2, wherein the inner wall 26 of the second sleeve 17 forms a sliding surface for the locking bodies 12. In the fixing position 8, the locking bodies 12 abut against the inner wall 26 of the second sleeve 17. In this case, the inner diameter of the second sleeve 17 is selected such that the locking bodies 12 are held in the openings 11 of the first sleeve 10 and in the recess 13 of the striker pin 3, so that the striker pin 3 is locked relative to the first sleeve 10.

When the impact instrument 1 is placed on an implant to be joined and a force is exerted onto the impact instrument 1, the striking piece 6 moves the first sleeve 10 and the striker pin 3 that is locked to the first sleeve 10 relative to the housing 2 in the axial direction. The striking piece 6 thereby moves in axial direction into the housing 2.

The second sleeve 17 is provided with a cross-section expansion 14, wherein the inner diameter of the second sleeve 17 increases in the area of the cross-section expansion 14, wherein the cross-section expansion 14 is configured to partially accommodate the locking bodies 12 in the release position 9.

If the striking piece 6 is axially moved this far into the housing 2, the locking bodies 12 reach the area of the cross-section expansion 14 in the release position 9. Thereby, the locking bodies 12 slide out of the recess 13 of the striker pin 3 and into the opening 11 of the first sleeve 10 and the cross-section expansion 14 of the second sleeve 17. This causes the striker pin 3 to be released abruptly and accelerated by the first spring element 4 in the direction of the striking piece 6.

The first sleeve 10 has a receiving part 15 for the striking piece 6 on one end face, wherein the receiving part 15 is designed such that the striker pin 3 directly contacts the striking piece 6 in the release position 9. For this purpose, the first sleeve 10 has an opening 25 on the end face.

The striker pin 3 is provided with a circumferential collar 16, wherein the first spring element 4 bears against the collar 16 and against the housing 2.

The second sleeve 17 is accommodated in the housing 2 in an axially movable manner. A second spring element 18 positions the second sleeve 17 relative to the housing 2.

Furthermore, a third spring element 19 is provided, which is arranged on the side of the end face between the first sleeve 10 and the housing 2 and causes the first sleeve 10 and the striking piece 6 to be returned in the release position 9.

The housing 2 has a handpiece 20 on the end face facing away from the striking piece 6. The handpiece 20 may be formed of plastic or metal.

A sealing element 21 is provided between the housing 2 and the striking piece 6.

On the end face facing the striker pin 3, the striking piece 6 has a projection which projects through the opening 25 made in the end face of the first sleeve 10.

FIG. 1 shows the impact instrument 1 in its initial position. The striking piece 6 and the striker pin 3 are spaced apart from each other. The locking bodies 12 are located in the opening 11 of the first sleeve 10 and in the recess 13 of the striker pin 3. The locking bodies 12 bear against the inner wall 26 of the second sleeve 17. As a result, the first sleeve 10 and the striker pin 3 are locked with each other.

Figure 2:
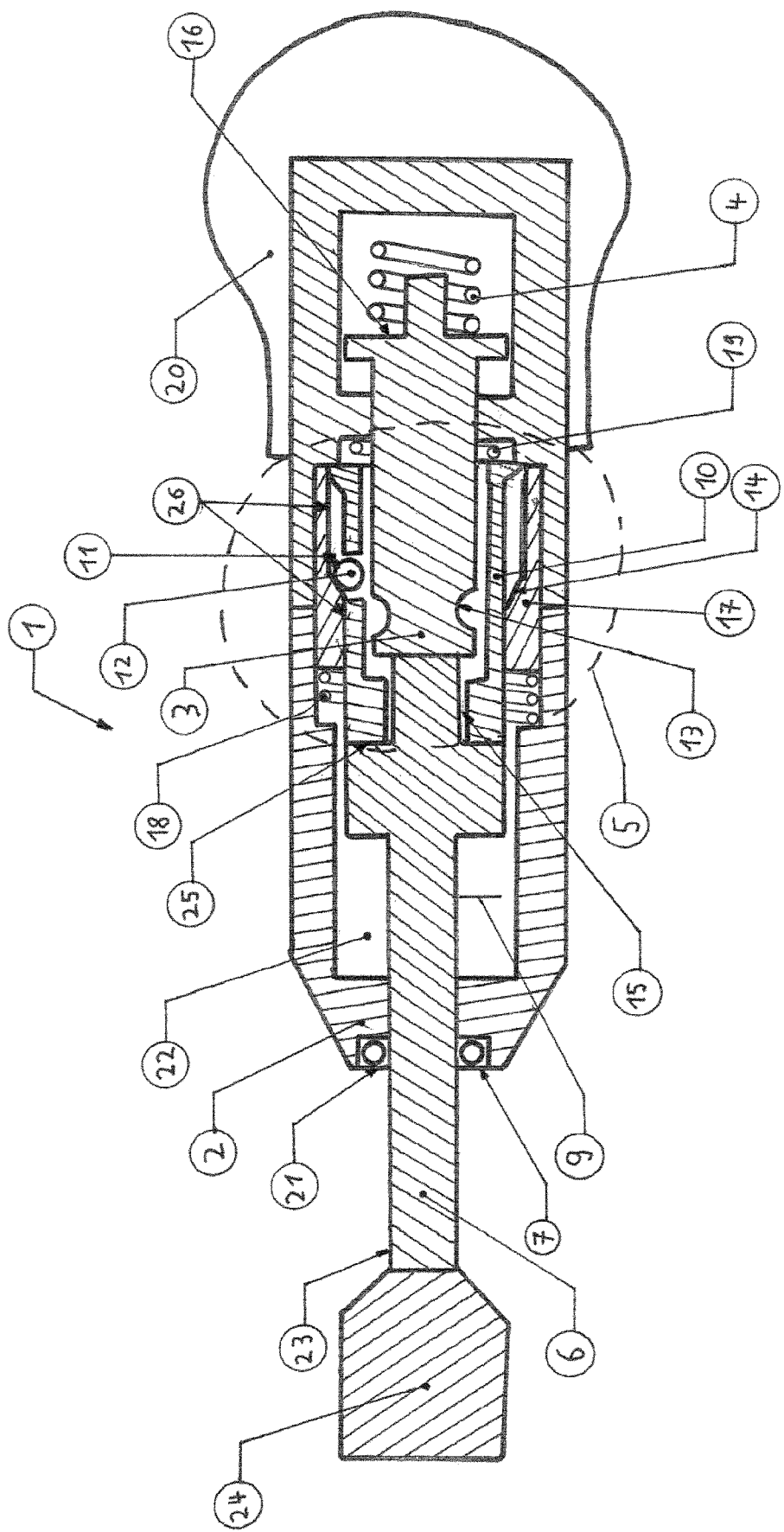
FIG. 2 a cross-section view of the impact instrument in the release position.

FIG. 2 shows the impact instrument 1 after it has been placed on an implant component to be joined and a force has been exerted axially onto the impact instrument 1 via the handpiece 20. The exertion of force in the axial direction causes the striking piece 6 to move relative to the housing 2, wherein the striking piece 6 takes along the first sleeve 10 and the locking members 12 disposed therein. As a result of the fact that the striker pin 3 is locked with the first sleeve 10 via the locking bodies 12, the striker pin 3 also moves in the same way.

In the position shown in FIG. 2, the cross-section expansion 14 of the second sleeve 17 has been reached and the locking bodies 12 slide out of the recess 13 of the striker pin 3 and release the striker pin 3. By moving the striking piece 6, the first sleeve 10 and the striker pin 3, the first spring element 4 has been preloaded so that the striker pin 3, after being released by the locking bodies 12 sliding out of the recess 13, is accelerated towards the striking piece 6.

After release, the striker pin 3 is accelerated by the spring element 4. The accelerated striker pin 3 contacts the front face of the striking piece 6 directly and at high velocity. Together with the pre-force required to release the release device 5, an impulse is introduced into the striking piece 6, which in turn is introduced into the implant component to be joined via the free end 23. For better contacting of the implant component, the striking piece 6 has a contacting element 24 at the free end 23, which is provided with a conical recess on the side facing the implant component. This ensures at least a ring-shaped contact of the striking piece 6 with the implant component to be joined. Due to the initial force required to release the release device 5, the impact instrument 1 or the contacting element 24 of the striking piece 6 rests with a preload on the implant component to be joined. In this way the impulse introduced into the striking piece 6 via the striker pin 3 can be transferred completely onto the implant component to be joined. This allows a predetermined and reproducible impulse to enter an implant component.

During the acceleration of the striker pin 3, the striker pin 3 moves in an axial direction relative to the first sleeve 10, the second sleeve 17 and the striking piece 6. In this position, the recess 13 of the striker pin 3 is displaced in the axial direction towards the locking bodies 12. The locking bodies 12 remain in the opening 11 of the first sleeve 10 and in the cross-section expansion 14 of the second sleeve 17.

If the impact instrument 1 is now unloaded, the striking piece 6 moves out of the housing 2 again. Thereby, the spring elements 18, 19 relax, wherein the third spring element 19 causes the first sleeve 10 to move together with the striking piece 6 in axial direction and, in doing so, the first sleeve 10 to abut against the end face of the striking piece 6. The second spring element 18, in turn, causes the second sleeve 17 to move in the opposite direction until the opening 11, the locking bodies 12 and the recess 13 are aligned, thereby causing the locking bodies 12 to slide back into the recess 13, thereby locking the striker pin 3 with the first sleeve 10.

Thus, the components of the impact instrument 1 automatically move back to the initial position shown in FIG. 1 after the impact and release. The impact instrument 1 can be used immediately for another impact. It is not necessary to preload the device manually or the like.

What is claimed is:

1. An impact instrument for joining prosthetic implants, comprising:
   a housing,
   a striker pin,
   a first spring element associated with the striker pin,
   a release device comprising a first sleeve and at least one locking body, and
   a striking piece, wherein the housing accommodates the striker pin, the first spring element, the release device, and at least part of the striking piece so that the striking piece projects from the housing at an end face thereof, wherein the first sleeve is arranged in the housing in an axially movable manner and accommodates the striker pin, wherein the first sleeve has at least one opening on its circumference in which the at least one locking body is arranged, wherein the release device is movable between a fixing position and a release position, wherein the striker pin is spaced apart from the striking piece and locked with the first sleeve by the at least one locking body in the fixing position, wherein when the striking piece moves axially into the housing, an end face of the striking piece abuts and pushes an end face of the first sleeve to move the release device from the fixing position to the release position in which the at least one locking body moves out of engagement with the striker pin and outwardly into a cross-section expansion to release the striker pin so that the striker pin moves toward and impacts the striking piece, accelerated by the first spring element.

2. The impact instrument according to claim 1, wherein when the impact instrument is placed on an implant to be joined, the housing moves in an axial direction towards the implant so that the striking piece moves into the housing, wherein the striker pin is released as soon as the release device reaches the release position.

3. The impact instrument according to claim 1, wherein in the striker pin, at least one recess is provided, which accommodates the at least one locking body in the fixing position.

4. The impact instrument according to claim 3, wherein the at least one recess is a circumferential groove in a circumference of the striker pin.

5. The impact instrument according to claim 3, wherein the at least one locking body abuts against an inner wall of the housing in the fixing position, wherein an inner diameter of the housing is selected such that the at least one locking body is held in the at least one opening of the first sleeve and in the at least one recess of the striker pin and thereby the striker pin is locked relative to the first sleeve.

6. The impact instrument according to claim 5, wherein the striking piece axially moves the first sleeve and the striker pin locked with the first sleeve in the housing when the striking piece axially moves into the housing.

7. The impact instrument according to claim 3, wherein an inner diameter of the housing increases in a region of the cross-section expansion, wherein the cross-section expansion is designed to partially accommodate the at least one locking body in the release position.

8. The impact instrument according to claim 7, wherein the at least one locking body, in the release position, moves out of engagement with the striker pin by sliding out of the at least one recess of the striker pin and into the cross-section expansion, so that the striker pin is released.

9. The impact instrument according to claim 1, wherein the first sleeve has, on the end face of the first sleeve, a receiving part for the striking piece that allows the striker pin to directly contact the striking piece in the release position.

10. The impact instrument according to claim 1, wherein the striker pin is provided with a circumferential collar, wherein the first spring element bears against the circumferential collar and against the housing.

11. The impact instrument according to claim 1, wherein a second sleeve is arranged between the first sleeve and the housing, wherein an inner wall of the second sleeve forms a sliding surface for the at least one locking body and wherein the second sleeve comprises the cross-section expansion.

12. The impact instrument according to claim 11, wherein the second sleeve is accommodated in the housing in an axially movable manner and a second spring element is provided, which positions the second sleeve relative to the housing.

13. The impact instrument according to claim 1, wherein a third spring element is provided, which is arranged between the first sleeve and the housing on an end of the first sleeve opposite the end face of the first sleeve.

14. The impact instrument according to claim 1, wherein the housing is provided with a handpiece.

* * * * *